US009271479B2

(12) United States Patent
Cote-Sierra et al.

(10) Patent No.: US 9,271,479 B2
(45) Date of Patent: Mar. 1, 2016

(54) INFLAMMATION IN VIVO MODEL

(71) Applicant: Hoffmann-La Roche Inc., Nutley, NJ (US)

(72) Inventors: Javier Cote-Sierra, Chapel Hill, NC (US); Antonio Iglesias, Freiburg (DE); Claas Aiko Meyer, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/476,626

(22) Filed: Sep. 3, 2014

(65) Prior Publication Data

US 2015/0026832 A1 Jan. 22, 2015

Related U.S. Application Data

(63) Continuation of application No. 13/867,263, filed on Apr. 22, 2013, now abandoned, which is a continuation of application No. PCT/EP2011/068696, filed on Oct. 26, 2011.

(30) Foreign Application Priority Data

Oct. 29, 2010 (EP) .................................... 10189446

(51) Int. Cl.

| | |
|---|---|
| ***A01K 67/027*** | (2006.01) |
| ***G01N 33/00*** | (2006.01) |
| ***C12N 5/10*** | (2006.01) |
| ***C12N 15/85*** | (2006.01) |
| ***A61K 49/00*** | (2006.01) |
| ***G01N 33/50*** | (2006.01) |

(52) U.S. Cl.

CPC ......... *A01K 67/0276* (2013.01); *A01K 67/0275* (2013.01); *A61K 49/0008* (2013.01); *C12N 15/85* (2013.01); *G01N 33/502* (2013.01); *G01N 33/5088* (2013.01); *A01K 2227/105* (2013.01); *A01K 2267/035* (2013.01); *A01K 2267/0368* (2013.01); *G01N 2500/10* (2013.01)

(58) Field of Classification Search

CPC .............. A61K 38/20; A01K 227/105; A01K 2267/035; A01K 67/0275; A01K 67/0276; C12N 15/85; C12N 15/8509

USPC ........................................ 800/18, 3; 435/325

See application file for complete search history.

(56) References Cited

PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Munoz et al. (2009) Stem Cell Rev. and Rep., vol. 5, 6-9.*
Oboki et al. (2010) PNAS, vol. 107(43)18581-18586, including Supplement 1 (S1), pp. 1-12.*
Carriere et al. (2007) PNAS, vol. 104(1), 282-287.*
Palmer et al. (2008) Cytokine, vol. 42, 358-364.*
Cayrol et al., "The IL-1-like Cytokine IL-33 is inactivated after maturation by caspase-1" Proceedings of the National Academy of Sciences 106(22):9021-9026 (Jun. 2, 2009).
Carriere et al., "IL-33, the IL-1-like cytokine ligand for ST2 receptor, is a chromatin-associated nuclear factor in vivo" Proceedings of the National Academy of Sciences 104(1):282-287 (Jan. 2, 2007).
Clark et al., "A future of transgenic livestock" Nature Reviews: Genetics 4:825-833 (Oct. 2003).
Haraldsen et al., "Interleukin-33-Cytokine of dual function or novel alarmin?" Trends in Immunology 30(5):227-233 (May 1, 2009).
Moussion et al., "The IL-1-Like Cytokine IL-33 is Constitutively Expressed in the Nucleus of Endothelial Cells and Epithelial Cells In Vivo: A Novel 'Alarmin'?" PLoS One 3(10):1-8 (Jan. 1, 2008).
Munoz et al., "Constraints to Progress in Embryonic Stem Cells from Domestic Species" Stem Cell Rev and Rep 5:6-9 ( 2009).
Niemann et al., "Transgenic farm animals: present and future" Rev. Sci. Tech. Off. Int. Epiz. 24(1):285-298 ( 2005).
Oboki et al., "IL-33 is a crucial amplifier of innate rather than acquired immunity" Proceedings of the National Academy of Sciences 107(43):18581-18586 (Oct. 26, 2010).
Oboki et al., "IL-33 and IL-33 receptors in host defense and diseases" Allergology International 59(2):143-160 ( 2010).
Oboki et al., "Si Methods—Generation of IL-33-Deficient Mice" PNAS 107(43 Suppl S1):1-12 ( 2010).
Palmer et al., "The IL-1 receptor accessory protein (AcP) is required for IL-33 signaling and soluble AcP enhances the ability of soluble ST2 to inhibit IL-33" Cytokine 42(3):358-364 (Jun. 1, 2008).
Prelle et al., "Pluripotent Stem Cells—Model of Embryonic Development, Tool for Gene Targeting, and Basis of Cell Therapy" Anat. Histol.Embryol. 31:169-186 ( 2002).
Roussel et al., "Molecular Mimicry Between IL-33 and KSHV for attachment to Chromatin Through the H2A-H2B Acidic Pocket" EMBO Reports 9(10):1006-1012 (Oct. 1, 2008).
Wheeler et al., "Transgenic Technology and Applications in Swine" Theriogenology 56:1345-1369 ( 2001).

* cited by examiner

*Primary Examiner* — Anne Marie S Wehbe
(74) *Attorney, Agent, or Firm* — Jennifer K. Holmes

(57) ABSTRACT

The present invention relates to a non-human animal deficient in the N-terminal domain of the IL-33 gene. Also provided herein is the use of said non-human animal as an in vivo model of inflammatory diseases, especially with regard to screening methods for anti-inflammatory compounds, and methods for evaluating and optimizing the pharmacological properties of a given anti-inflammatory compound.

6 Claims, 8 Drawing Sheets

INFLAMMATION IN VIVO MODEL

CROSS REFERENCE TO RELATED APPLICATIONS

This application is a continuation of U.S. application Ser. No. 13/867,263, filed Apr. 22, 2013, which is a continuation of International Application No. PCT/EP2011/068696 having an International Filing date of Oct. 26, 2011, the entire contents of which are incorporated herein by reference, and which claims benefit under 35 U.S.C. §119 to European Patent Application No. 10189446.7 filed Oct. 29, 2010.

SEQUENCE LISTING

The instant application contains a Sequence Listing submitted via EFS-Web and hereby incorporated by reference in its entirety. Said ASCII copy, created Jun. 6, 2013, is named P4670C1_Corrected_Sequence_listing.txt, and is 28.128 bytes in size.

FIELD OF THE INVENTION

The present invention relates to a non-human animal deficient in the N-terminal domain of the IL-33 gene. Also provided herein is the use of said non-human animal as an in vivo model of inflammatory diseases, especially with regard to screening methods for anti-inflammatory compounds, and methods for evaluating and optimising the pharmacological properties of a given anti-inflammatory compound.

BACKGROUND OF THE INVENTION

The interleukin 33 (IL-33) cytokine is the newest member of the interleukin 1 (IL-1) family. Because of its nuclear localization, it was originally described as "Nuclear Factor from High Endothelial Venules". IL-33 is primarily expressed by fibroblasts and epithelial, endothelial and airway smooth muscle cells. IL-33 is the ligand for the IL-1 receptor-related protein ST2. The ST2 receptor is expressed in almost all innate immune cells (mast cells, basophils, eosinophils, neutrophils, natural killer (NK) cells and macrophages) and in NK T and T helper (Th) 2 cells. The interaction of IL-33 with ST2 on targeted cells can trigger the expression and secretion of pro-inflammatory, Th1, Th2 and Th17 cytokines and expression of chemokines involved in Th1, Th2 and innate immune effector functions (published papers and Hicks et al. manuscript in preparation). IL-33 binds to its specific surface receptor through its pro-inflammatory cytokine domain. In addition, IL-33 also has a N-terminal domain that contains a typical DNA-binding helix-turn-helix motif. In its nuclear uncleaved form, IL-33 interacts with histones 2A and 2B in heterochromatin promoting chromatin compaction and functioning as a potential transcriptional repressor. There is strong support showing that IL-33 is similar to other chromatin-associated cytokines (IL-1α and HMGB1) that appears to exert a dual-function, regulating transcriptional repression in the nucleus and signaling via a classic receptor acting as a potent pro-inflammatory cytokine Thus, it has been proposed that similarly to HMGB1, IL-33 may function as an 'alarmin' belonging to the larger family of damage-associated molecular pattern (DAMP) molecules.

The IL-33/ST2 axis plays pivotal roles in the patho-physiology of human inflammatory diseases as confirmed by their high levels of expression in diseased tissues. Elevated levels of either IL-33 and/or its soluble receptor ST2 are observed in rheumatoid arthritis (RA), inflammatory bowel disease (IBD), psoriatic and ulcerative colitis, acute eosinophilic pneumonia, severe asthma, idiopathic pulmonary fibrosis, liver fibrotic diseases, atopic dermatitis, systemic sclerosis, autoimmune and trauma patients. Similar to its role in humans, the IL-33/ST2 axis has been shown to be critical in murine inflammatory models. IL-33 exacerbates collagen-induced arthritis (CIA), allergic conjunctivitis and experimental autoimmune encephalomyelitis (EAE), Interruption of IL-3/ST2 signaling with antibodies has been shown to be beneficial for the resolution of allergic airway inflammation and bleomycin-induced lung injury. It has also been shown recently that IL-33 is up-regulated in an IBD mouse model of chronic intestinal inflammation (Oboki et al, PNAS 2010 107 (43) 18581-18586).

SUMMARY OF THE INVENTION

The non-human animal may be any non-human animal. Preferably, the non-human animal is a mammal, more preferably a rodent such as rat or a mouse, most preferably, the non-human animal is a mouse. In a preferred embodiment, said non-human animal is a mouse and the N-terminal deletion of the IL-33 gene comprises a deletion of the full DNA binding domain at the N-terminus of the IL-33 gene. Preferably, said N-terminal deletion of the IL-33 gene in the mouse comprises a deletion of amino acids 1-67 of the expression product of the IL-33 gene.

The non-human animal may be heterozygous or homozygous for the N-terminal IL-33 deletion. Preferably, the non-human animal is heterozygous for the N-terminal IL-33 deletion.

The non-human animal deficient in the N-terminus of the IL-33 gene according to the present invention displays the typical characteristics of inflammatory diseases. For instance, a mouse according to the present invention has such characteristics as normal birth rate and growth until about 3-4 months of age, then hemorrhagic lesions in ears and repeatedly observed large coagula in the thoracic cavity, smaller size and general ill picture. On pathological examination these mice reveal multiorgan inflammation, including chronic, multifocal myocarditis; chronic, suppurative, strong ileitis with enlarged intestinal walls; chronic utreteritis with marked hydronephrosis and kidney atrophy, moderate multifocal and perivascular infiltrates in the lung, splenic hyperplasia with strong expansion of eosinophils and macrophages in immune organs, lung and intestine.

Since the non-human animal according to the present invention exhibits an inflammatory phenotype, it is useful as an in vivo inflammation model. This non-human animal with an N-terminal IL-33 deletion can serve to practically prove the causal relationship between IL-33 dysfunctions and inflammatory disorders and allow the design of directed therapeutic strategies aimed to reduce or abolish the abnormal overproduction of IL-33 in patients. As massive production and secretion of IL-33 into the extracellular compartment is the cause of this severe inflammatory condition, this novel and unique non-human animal model can also be used to evaluate the in vivo efficacy and potency of IL-33 drug candidates if cross-reactivity with the non-human IL-33 or its receptor ST2 is given. Hence in a second object of the invention, said non-human test animal is used as an in vivo model of inflammatory diseases, especially with regard to screening for anti-inflammatory compounds. In one embodiment a method for screening for anti-inflammatory compounds is provided, comprising administering a candidate compound to a non-human animal with a N-terminal IL-33 deletion according to the present invention. In one embodiment, said method comprises a) providing the non-human animal with a N-terminal IL-33 deletion, b) administering to said non-human animal a candidate compound, c) comparing the inflammation symptoms of said non-human animal to those of a non-human animal with a N-terminal IL-33 deletion not administered said compound; wherein the compound that alleviates said inflammation symptoms is selected as an anti-inflammatory compound.

Candidate compounds include, but are not limited to small molecules, (poly) peptides, (glyco) proteins, antibodies or antibody fragments, (poly) or (oligo) nucleotides, nucleosides, lipids, combinations thereof and modified derivatives thereof.

Methods of administration of a candidate compound to be screened include, but are not limited to, oral administration and parenteral administration (e.g. intravenous administration, intraperitoneal administration and intranasal administration). In case of oral administration a candidate agent may be blended in a feed for administration.

The candidate agent may be administered in combination with a pharmaceutically acceptable conventional excipient (such as carrier and diluent) or additives. Further, the candidate agent may be encapsulated in, or bound (or attached) to, liposomes (e.g. positively charged liposomes) or nano-particles and administered.

Evaluation can be conducted for example using mitigation or recovery of inflammation symptoms, increase in body weight, recovery from hypertrophy of the ileon, or the like, as an indication, by observation with naked eye, measurement of body weight, histopathological observation (e.g. microscopic observation after tissue staining) and FACS analysis (see Examples below).

Through use of the subject animals with a N-terminal IL-33 deletion or cells derived there from, one can identify ligands or substrates that bind to, modulate, antagonize or agonize cellular IL-33. Of particular interest are screening assays for anti-inflammatory compounds that have a low toxicity for human cells. A wide variety of assays may be used for this purpose, including in vivo studies, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived there from. Cells may be freshly isolated from an animal, or may be immortalized in culture.

In another embodiment of the invention, said in vivo model is used for evaluation of the pharmacological effects such as in vivo efficacy and potency of IL-33 drug candidates. Therefore in another embodiment of the invention a method for evaluation of the pharmacological effects of a IL-33 drug candidate is provided, said method comprising administering said IL-33 drug candidate to a non-human animal with a N-terminal IL-33 deletion according to the present invention.

The present invention also relates to descendants of the non-human animals with an N-terminal IL-33 deletion as provided by the invention, obtained by breeding with the same or with another genotype. Preferably, the descendant is obtained by breeding with the same genotype. Said descendant comprises an N-terminal IL-33 deletion as the non-human animal with an N-terminal IL-33 deletion described above. A further object of the invention is the use of said descendants as an in vivo model of inflammatory diseases. In one embodiment, said descendants are used as an in vivo model for screening of anti-inflammatory compounds. In another embodiment, said descendants are used as an in vivo model for evaluation of the pharmacological effects of an anti-inflammatory compound.

Furthermore, the present invention relates to a cell line or primary cell culture derived from a non-human animal with an N-terminal IL-33 deletion or its descendants as described above.

In addition, the present invention also provides a tissue or an organ explant or culture thereof, derived from a non-human animal with an N-terminal IL-33 deletion or its descendants as described above.

The present invention also provides a tissue or cell extract derived a non-human animal with an N-terminal IL-33 deletion or its descendants as described above.

In another embodiment of the invention, above-mentioned cell line or primary cell culture, tissue or an organ explant or culture thereof, tissue or cell extract derived from a non-human animal with an N-terminal IL-33 deletion or its descendants is used as a model of inflammatory diseases. In one embodiment, said model of inflammatory diseases is used for screening of anti-inflammatory compounds, in another embodiment, said model of inflammatory diseases is used for or evaluation of the pharmacological effects of an anti-inflammatory compound, as outlined above.

DETAILED DESCRIPTION OF THE PREFERRED EMBODIMENTS

Definitions

Methods for producing a non-human animal with a deletion in a gene, such as the N-terminus of the IL-33 gene, are well known in the art. Suitable methods are described i.e. in Hogan B et al: Manipulating the mouse embryo, A laboratory manual, 2nd Edition (1994), Cold Spring Harbor Laboratory Press.

The term "IL-33 gene" as used herein relates in particular to the interleukin 33 gene also known as DVS27; NF-HEV; NFEHEV; C9orf26; DKFZp586H0523; RP11-575C20.2; IL33, IL-1F11, 9230117N10Rik, RGD1311155 and the like. Said gene comprises a N-terminal domain with a putative DNA-binding helix-turn-helix motif and a C-terminal cytokine domain. The IL33 gene is conserved in humans, chimpanzee, dog, cow, mouse, and rat. By way of an example the DNA sequence of the mouse IL-33 gene is depicted in SEQ ID. 1. The term "expression product of the IL-33 gene" refers to the translated protein of the IL-33 gene, i.e. the IL-33 protein.

"N-terminal IL-33 deletion" as used herein means that all or part of the N-terminus of the IL-33 gene is modified (for example substituted, deleted, added and/or inserted) or disrupted, whereby the expression product of the IL-33 gene lacks the whole or parts of the N-terminal domain and/or does not exhibit the function of the N-terminal domain. The N-terminal domain as used herein comprises a putative helix-turn-helix motif which is responsible for DNA binding and nucleon localization of IL-33. In a preferred embodiment the non-human animal is a mouse and amino acids 1-67 of the mouse expression product of the IL-33 gene (IL-33 protein) are modified or disrupted.

Such non-human animal is depicted herein as a non-human animal with a N-terminal IL-33 deletion, or a non-human animal deficient in the N-terminus of the IL-33 gene or a N-terminal IL-33 gene knock-out non-human animal and the like. In one special preferred embodiment said modification of the N-terminus of the IL-33 gene is achieved through knock-in of a DsRed cassette, thus deleting the N-terminal part of the IL-33 gene. Said non-human animal is accordingly also referred to as DsRed-IL33/COOH non-human animal. The term "wild type" as used herein refers to a non-human animal having a full-length IL-33 gene.

"Non-human animal" as described herein refers to any animal that is not a human. Preferably, the non-human animal is a mammal, more preferably a rodent such as rat or a mouse, most preferably, the non-human animal is a mouse.

The non-human animal with a N-terminal IL-33 deletion as described above can be used as a model for treatment of inflammatory diseases. It allows to investigate the effect of an potentially non-inflammatory compound on the inflammatory disease in a non-human in vivo model. Since the transgenic animal is immunotolerant for the transgenic human mAb11 antibody, the effect of chronic treatment with a therapeutic antibody such as for example Mab 11 can be determined. Also, the effect on extracellular IL-33 levels and the process and kinetics of an inflammatory disease can be followed.

The term "inflammatory disease" as used herein relates to any impairment of health or a condition of abnormal functioning characterized by inflammation. In particular, the term "inflammatory disease" as used herein relates to diseases connected to an increased level of IL-33, for example, but not limited to inflammatory bowel disease, rheumatoid arthritis, urticuria, atherosclerotic vascular disease, psoriatic colitis, ulcerative colitis, acute eosinophilic pneumonia, severe asthma, idiopathic pulmonary fibrosis, liver fibrotic diseases, atopic dermatitis, systemic sclerosis, autoimmune diseases and the like.

"Anti-inflammatory compounds" as used herein means any molecule with the capability of reducing inflammatory responses, in detail, affecting the biological action of IL-33. As such, "Anti-inflammatory compound" includes, but is not limited to small molecules, (poly) peptides, (glyco) proteins, antibodies or antibody fragments, (poly) or (oligo) nucleotides, nucleosides, lipids, combinations thereof and modified derivatives thereof "Anti-inflammatory compound" also includes molecules that mediate RNA interference such as shRNA, microRNA, siRNA, antisense oligonucleotides, spiegelmers, LNA or PNA oligomers, or combinations thereof. Putative anti-inflammatory compounds as used herein are also depicted as "IL-33 drug candidates" or "candidate compounds".

EXAMPLES

The present invention will now be described in more detail by working examples, provided that the examples should not be interpreted as those limiting the scope of the present invention.

Example 1

Generation of a Targeting Vector

The targeting vector (SEQ ID. NO. 2) was generated using recombineering technology as supplied by Gene Bridges GmbH, Heidelberg. It contains the following elements:

| | |
|---|---|
| 1-70 | IL-33 exon 1b |
| 71-3871 | intron |
| 3872-3882 | IL-33 exon 2 |
| 3883-4557 | dsRed monomer CDS |
| 4558-4579 | IL-33 exon 3 |
| 4580-4590 | intronic sequence |
| 4591-4626 | lox site |
| 4625-6040 | neomycin selection cassette |
| 6041-6074 | lox site |
| 6075-6571 | intronic sequence |
| 6572-6682 | IL-33 exon 4 |
| 6683-7285 | intron |
| 7286-7603 | pBluescript SKII+ |
| 7604-8463 | diphteria toxin a selection cassette |
| 8464-10697 | pBluescript SKII+ |

The targeting vector was used for homologous recombination in BALB/c ES cells. Positive clones were identified using PCR screening strategies (sequences of oligonucleotides see below). Following electroporation of an Cre expressing plasmid site specific recombination leads to the removal of the neomycin selection cassette in vitro. After blastocyst injection of ES cell clones chimeric animals were breed and DNA preparations of biopsies of the F1 and F2 generation were used to confirm the identity of the targeted mutation as well as genotyping using PCR (PCR AB, CD, EF and EFG in FIG. 1*b*).

```
Oligonucletides
Oligonucletide A:
                                    (SEQ ID. NO. 3)
TAG AAA GAG CCC AGT GTT AAG C

Oligonucletide B:
                                    (SEQ ID. NO. 4)
GGC TTG CCC TCG CCC TCG
```

-continued

```
Oligonucletide C:
                                 (SEQ ID. NO. 5)
CAC CTG CGA CTT CAA GAC C

Oligonucletide D:
                                 (SEQ ID. NO. 6)
ACG ATT CCT TAG TGA TGG GGC

Oligonucletide E:
                                 (SEQ ID. NO. 7)
GTT GCT TCT GAT GAC TTC AGG

Oligonucletide F:
                                 (SEQ ID. NO. 8)
GCA ATA GCC CTT GCC AAG GC

Oligonucletide G:
                                 (SEQ ID. NO. 9)
TGC TGT TCC AGC CTC TGT TGG
```

Example 2

Generation of N-terminal IL-33 Knockout Mouse

Figure 1:
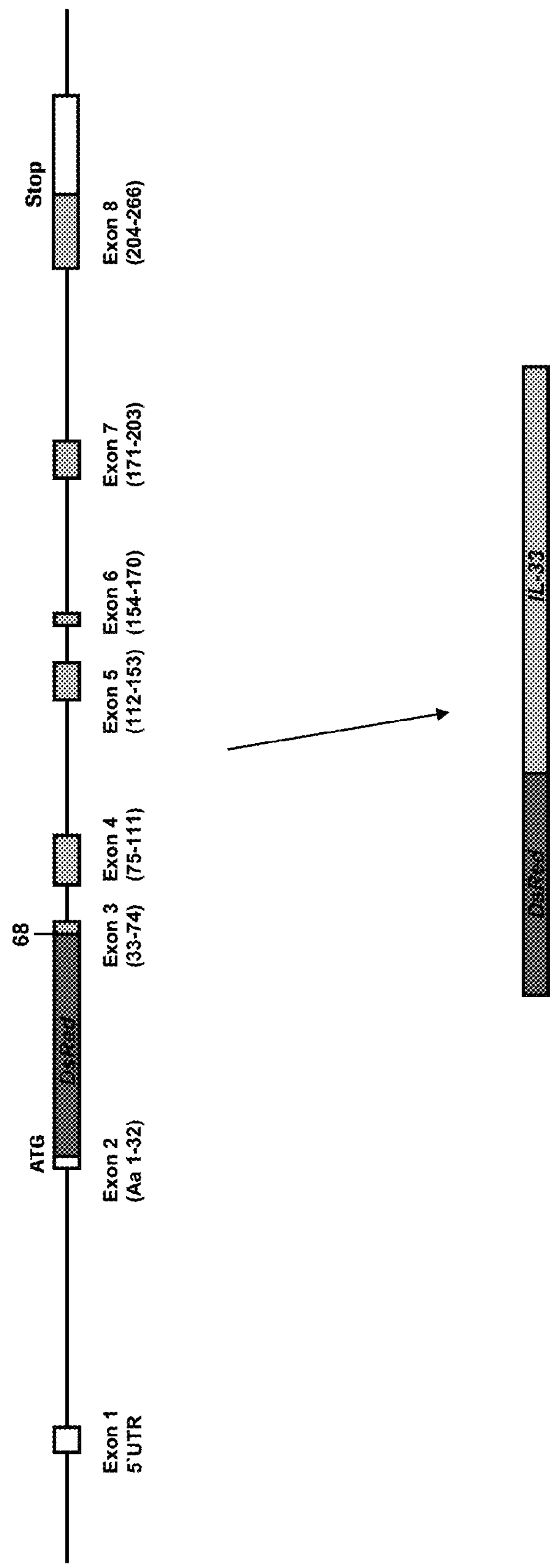
FIG. 1*a*: Schematic drawing of the targeted mutation of IL-33. The DsRed cassette was inserted at the Start codon and fused with IL-33 at its amino acid position 68.
FIG. 1*b*: Targeting strategy. RFP: red fluorescent protein; tm1: targeted mutation 1; wt: wild-type; Marker: marker X (Roche); kb: 1 kilo base pairs; EcoRI: Restriction endonuclease site; NeoR. Neomycin selection cassette; triangles: lox sites
Figure 1:
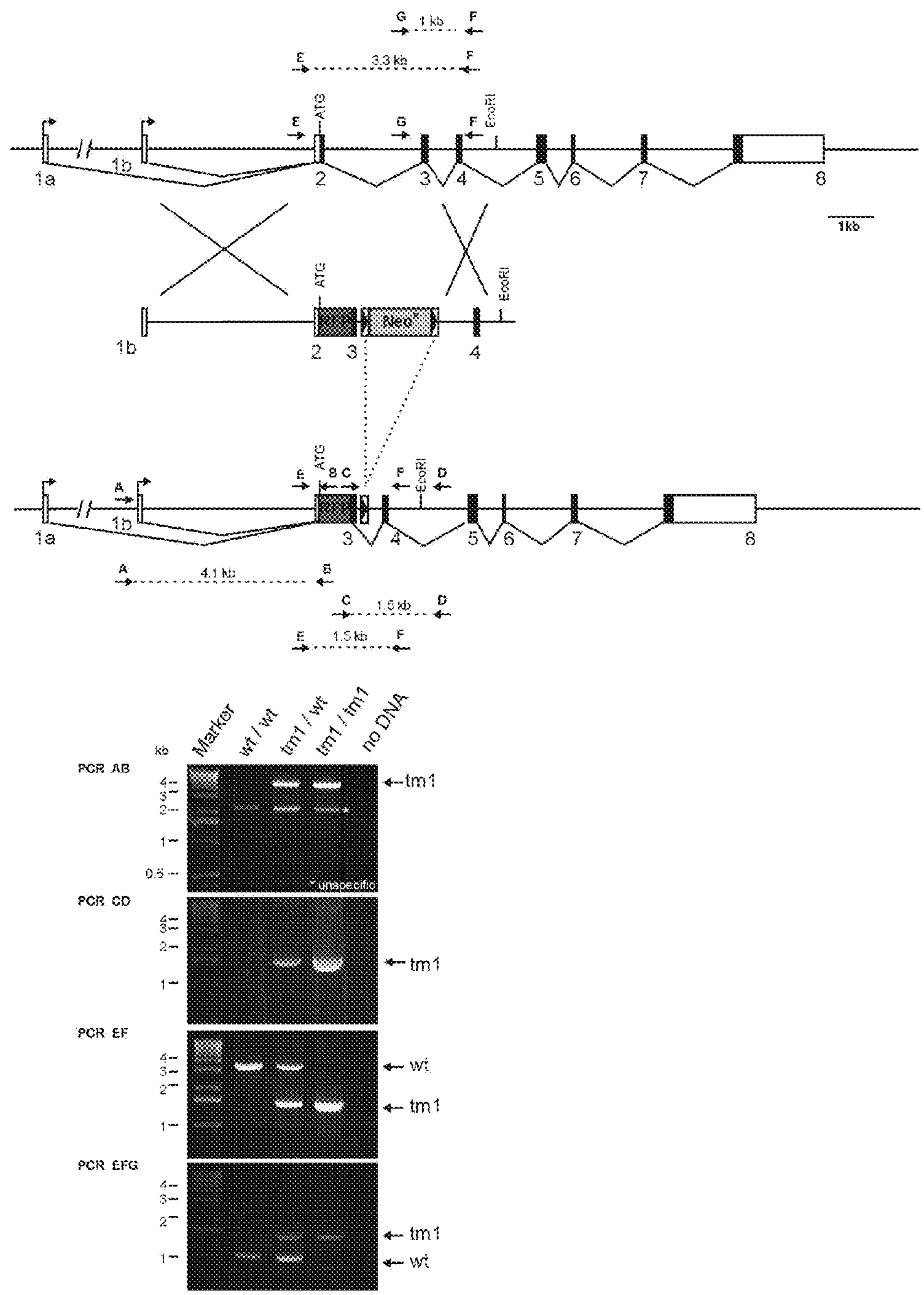
Figure 2:
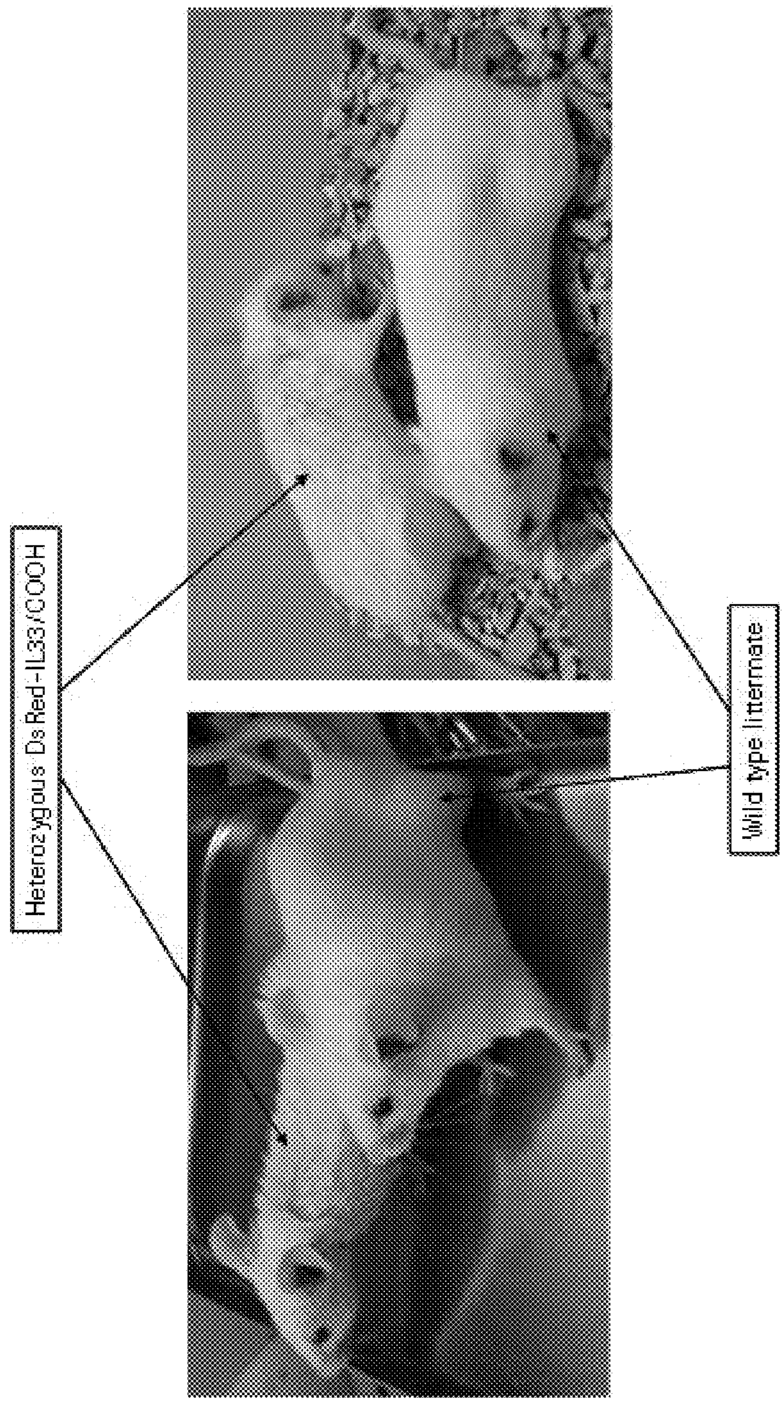
FIG. 2: Phenotype of heterozygous DsRedIL-33/COOH knock-in mice. Growth retardation, erected fur.
Figure 3:
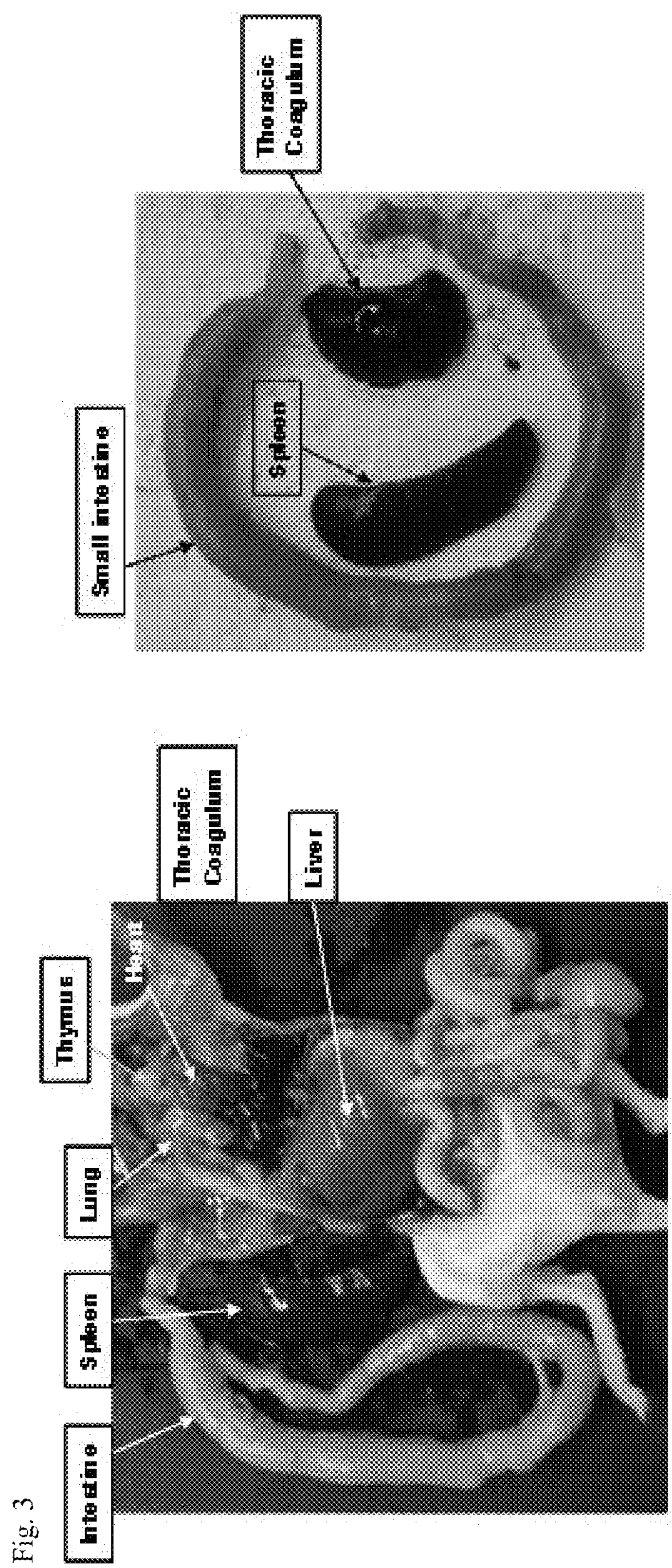
FIG. 3: Phenotype of heterozygous DsRedIL-33/COOH knock-in mice. Organ morphology.
Figure 4:
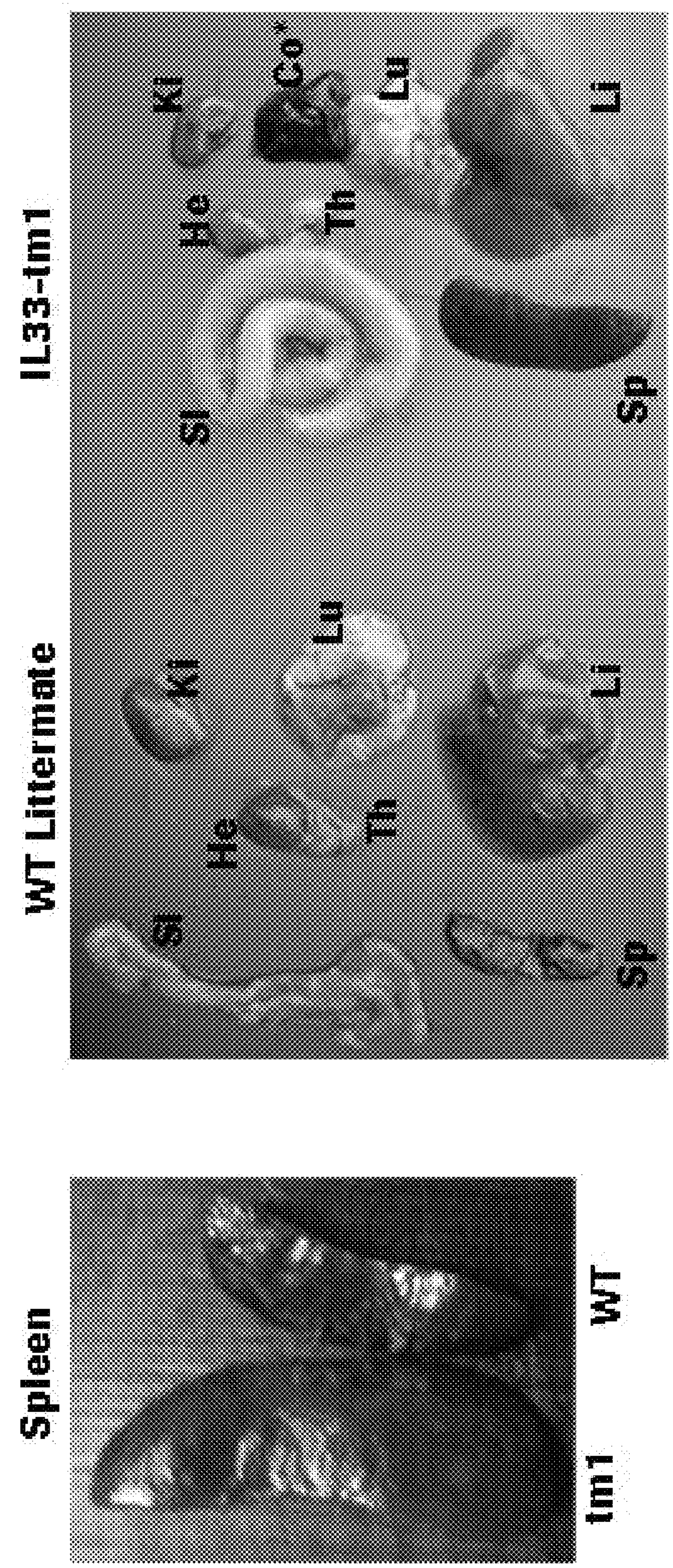
FIG. 4: Phenotype of heterozygous DsRedIL-33/COOH knock-in mice. Organ morphology compared to wild-type mouse. SI: small intestine; He: heart; Th: thymus; Ki: kidney; Lu: lung; Sp: spleen; Li: liver Co*: blood coagulum in thoracic cavity
Figure 5:
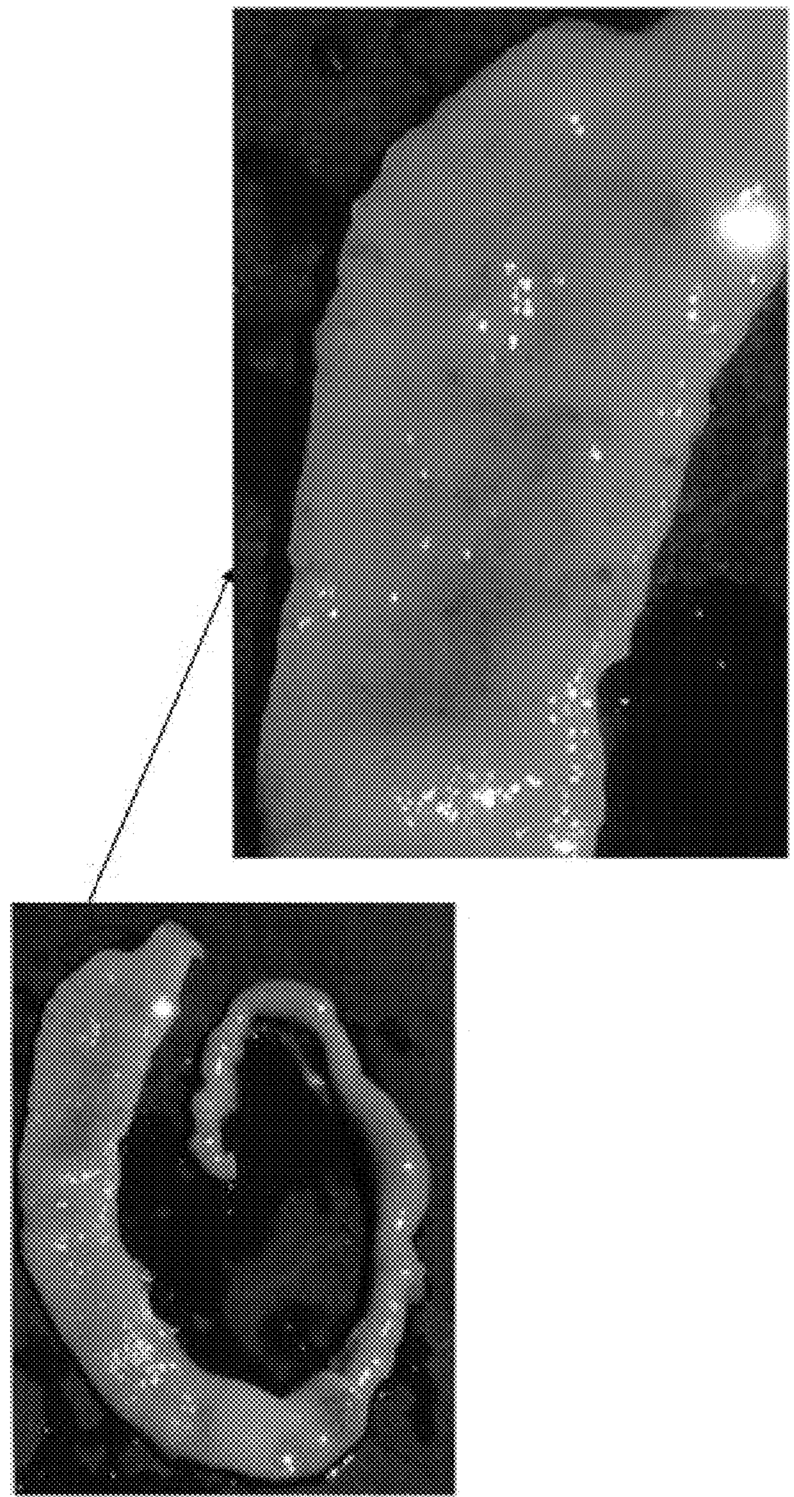
FIG. 5: Phenotype of heterozygous DsRedIL-33/COOH knock-in mice. Ileon hypertrophy. Intestine preparation opened longitudinally.

Two genetically modified knock-in mouse models in a Balb/c background were generated. The first mutant targets the N-terminal intracellular transcriptional factor-like activity by in-frame replacing it with the fluorochrome DsRd-monomer (DsRed-IL33/COOH) keeping the functional cytokine domain complete (FIG. 1). The second mutant replaces the pro-inflammatory cytokine domain by in-frame knocking-in the fluorochrome DsRed keeping the DNA binding domain intact (NH2/L33-DsRed).

Example 3

Characterization of N-terminal IL-33 Knockout Mouse

Figure 6:
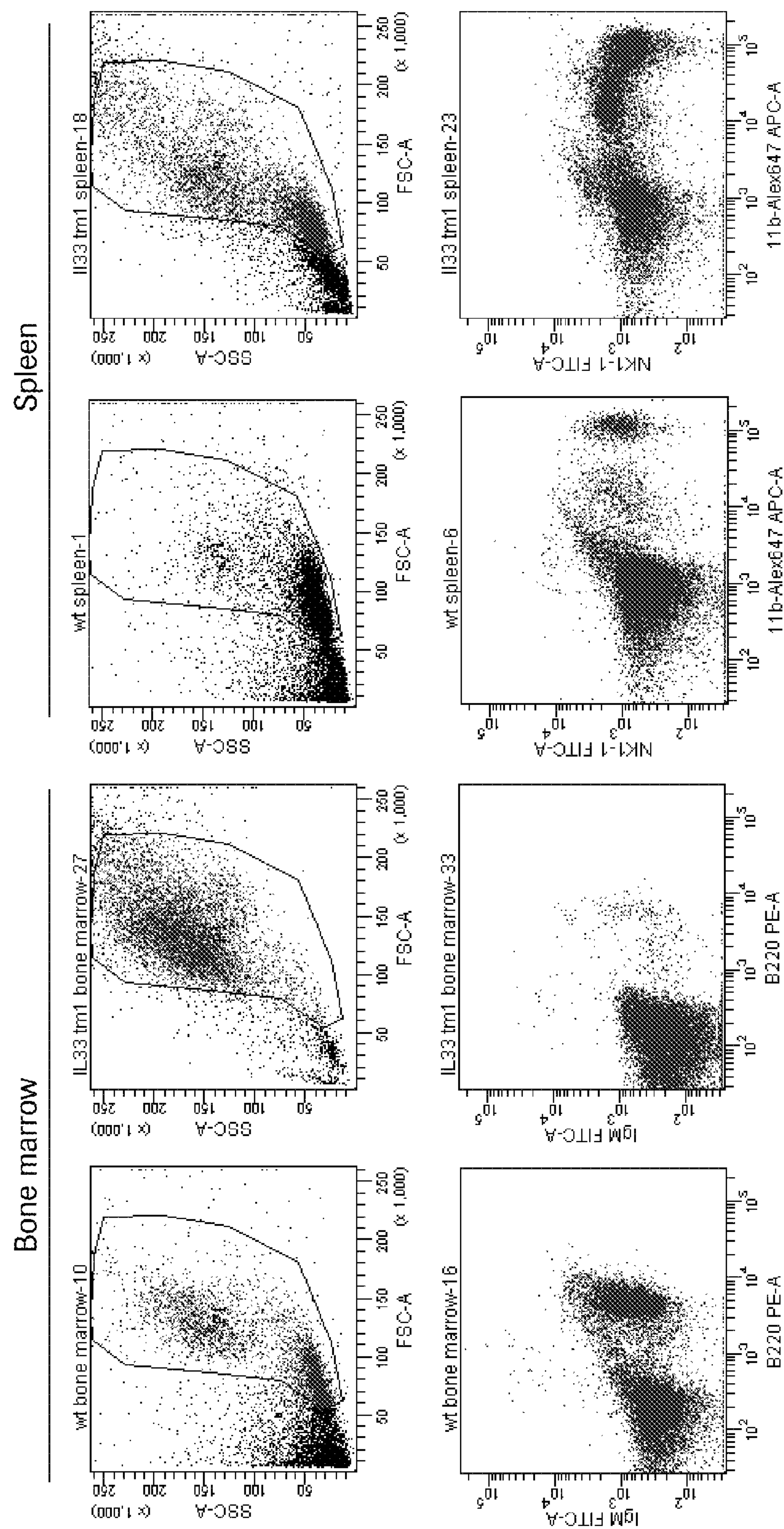
FIG. 6: Phenotype of heterozygous DsRedIL-33/COOH knock-in mice (DsRedIL-33/COOH-KI) via FACS analysis. Cell suspensions of the indicated organs were stained with antibodies specific for defined surface marker: CD45 (labeled APC-Cy7), total leukocytes; CD11b (labeled allophycocyanin, APC), macrophages; SiglecF (labeled phycoerythrin PE), eosinophils; Gr1 (labeled PE-Cy7), granulocytes; F4/80 (labeled Alexa 488), monocytes. Stained cells were acquired using a FACS Canto I device (BD Corp.) and analysed with FlowJo software. Y-axis: SiglecF, X-Axis: F4/80. Figures show the superposed stainings of different cell populations, DsRedIL-33/COOH knock-in mice have an increase in eosinophils as determined by high expression of SiglecF and F4/80 (see marked populations, "Eos"=Eosinophils)
Figure 7:
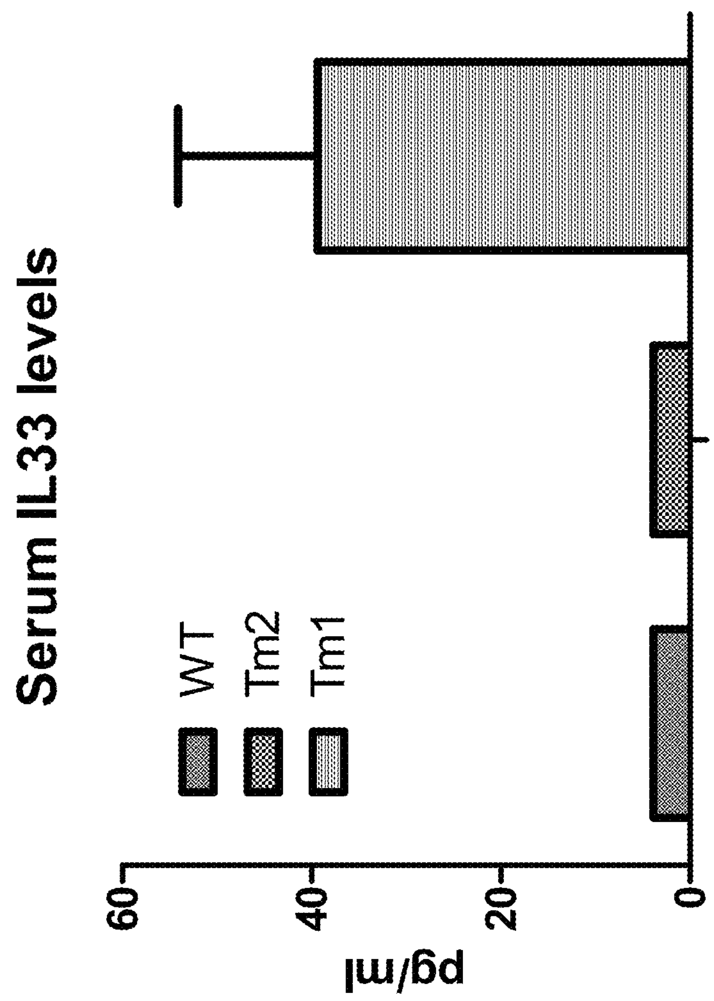
FIG. 7: Phenotype of heterozygous DsRedIL-33/COOH knock-in mice. Serum IL-33 levels.

Unexpectedly, the genetic engineered heterozygous mutant mice missing the IL-33 N-terminal domain but maintaining an active the proinflammatory cytokine activity in the cytoplasm (DsRed-IL33/COOH) die at around of 4 months of age. Apparently normal at birth, they become progressively sick and finally moribund between 4 and 5 months later with an estimated phenotype penetration of around 60%. At the age of 3-4 months, these mutants start displaying bloody lesions in ears and enlarged bellies. Upon necropsy, a massive splenomegaly, hypertrophy of the ilion suggestive of intestinal inflammation, the presence of large coagula in the thoracic cavity and kidney atrophy are repeatedly observed (FIGS. 2-5). Closer examination of different organs in FACS analysis showed a strong eosinophilia in lungs, spleen, lymph nodes, Payer's Patches and peripheral blood (FIG. 6). Serum IL-33 levels are elevated in DsRed-IL33/COOH knockout mice (FIG. 7).

Discussion

We have recently found that intranasal administration of IL-33 evoked profound lung inflammation with multinucleated giant cells of macrophage origin in the interstitium (Hicks et al. manuscript in preparation). In the same manner, IL-33 also evoked a bone marrow hyperplasia with big cluster of myeloid/granulocytic cells as shown by histopathology (Hicks et al. manuscript in preparation). In addition, high levels of soluble IL-33 are found in the plasma of peripheral blood of these mice, strongly suggesting that the immunopathological effects seen in our DsRed-IL33/COOH mutant animals is the result of the continuous presence of the fully active DsRed-IL33/COOH cytokine in the cytoplasm and its possible release into the extracellular compartment, thus behaving as a potent endogenous DAMP signal as it has been hypothesized.

This "alarmin"-like effect of knocking out the N-terminal domain of IL-33 is thus similar to human immune-pathological conditions (whose diagnosis remains unknown) when a potent danger signal is released after tissue damage, necrosis or autoimmunity. As the occurrence of severe multi-organ inflammation in patients with homozygous mutations or deletions of gene encoding IL-1RA and its blockade with mAbs have demonstrated the central role of IL-1$\alpha$ and IL-$\beta$ in a number of auto-inflammatory diseases (Weber at al, Science signaling, 3, 2010). Possibly genetic variations of IL-33 could result in over-expression and/or secretion of this possible "danger" molecule and it may contribute to the pathogenesis of auto-inflammatory or allergic diseases. Precisely, it has recently been shown a positive association between polymorphisms in the IL-33 gene and higher IL-33 levels with susceptibility of Japanese cedar pollinosis (Sakashita et al. Clin. Exp. Allergy December 2008).

What is claimed is:

1. A transgenic mouse comprising a deletion of at least one allele of the IL-33 gene, wherein the deletion is a deletion of amino acids 1-67 of the expression product of the IL-33 gene, and wherein the transgenic mouse expresses the expression product of the IL-33 gene with a deletion of amino acids 1-67.

2. A descendant of the transgenic mouse of claim 1, obtained by breeding with a transgenic mouse of the same genotype, and wherein the descendant expresses the expression product of the IL-33 gene with a deletion of amino acids 1-67.

3. A cell line or primary cell culture derived from the transgenic mouse of claim 1.

4. A tissue or an organ explant or culture thereof derived from the transgenic mouse of claim 1.

5. A method for screening for anti-inflammatory compounds, comprising:

a) providing a transgenic mouse comprising a deletion of at least one allele of the IL-33 gene;

b) administering to the transgenic mouse a candidate compound; and c) comparing the inflammation symptoms of the transgenic mouse to those of a transgenic mouse comprising a deletion of at least one allele of the IL-33 gene that was not administered said compound;

wherein the deletion of at least one allele of the IL-33 gene is a deletion of amino acids 1-67 of the expression product of the IL-33 gene and wherein a compound that alleviates said inflammation symptoms is selected as an anti-inflammatory compound.

6. A method for evaluating the pharmacological effects of an anti-inflammatory compound, comprising:

a) providing a transgenic mouse comprising a deletion of at least one allele of the IL-33 gene;

b) administering to the transgenic mouse a IL-33 drug candidate; and c) comparing the inflammation symptoms of the transgenic mouse to those of a transgenic mouse comprising a deletion of at least one allele of the IL-33 gene that was not administered said candidate;

wherein the deletion is a deletion of amino acids 1-67 of the expression product of the IL-33 gene.

* * * * *

SEQUENCE LISTING

```
<160> NUMBER OF SEQ ID NOS: 9

<210> SEQ ID NO 1
<211> LENGTH: 9371
<212> TYPE: DNA
<213> ORGANISM: Mus musculus

<400> SEQUENCE: 1

atgagaccta gaatgaagta ttccaactcc aagatttccc cggcaaagtt cagcagcacc      60

gcaggcgaag ccctggtccc gccttgcaaa ataagaagta agagcgctct ctttaaccac     120

tattaaatct attatcaaat atttgttatt tcaacatgaa gacgggcgac cttaccaaaa     180

actctcaagt atacaagagc tgaaaagaaa gagagacagc ttgttgtttt cttaaacaga     240

cttcacagca tcaccgttgt tatttggtac aacataggac agttgaccac ttattcttgg     300

actagtaaca agaagggtag cagagctctg gtggacagaa cggaagttag agggtgatgg     360
```

-continued gaaaggaaag cgatgtcccc ttctgccctt cccgaggtgc tggactgctc acacacttct 420
ttcaaagcca ggatttaaaa gaaaaaaaat tgacagtggt ttctgaatgg ccagaaaaaa 480
atcacagtta aattaatcct ttcatttgca gttatgtcat aatgctctgt gcagatataa 540
tgactcagtg caagtgactc ggtgttccca agtttcctcc tattaaagaa tgcactgtct 600
tcagatccaa gaaaacgagg ccctttatcg gcactgcctt gtggagtaga catgccagaa 660
tgcctgacat tggtgcccgc gcttgcttcg aatactgaga tcttacaatt cacatgttct 720
agttttcatc tccatctcac cctggaatac tatttacgat gtccagaaca caatggactt 780
ttctgcatgg gacttaaatt tttcttgggc taagtaaaat gagaattaac aaataactcg 840
ttaatctttt tagttccgtt gcctgaattt gcatttgact gctccctcag atggcagtgc 900
tcacttactt cttcccctac caaataagac tctgtgtagc tcacactgat ctggaaactc 960
gcaaccctcc tgctttagcc tcttgggtac tgggactaga ggcacgacca catctggcca 1020
gtggtccttt tctttgatgg aggtagagtc taatgagtag ctttgatatt aaagatattg 1080
cattaattaa ttttacaccg ctatggccaa atacccagca gaagcaacat aaaggcttca 1140
tagcttagaa gatacaggcc attaggatac agcagggatg gtggctgaac cagtttgatc 1200
tctggtagcc ttagcttcca gggacttctc atatggcacc gcccaagagt gggagatgaa 1260
ggaccaggct ataatctgag actgtccccc acggtctagg tatatcagca aggccccaaa 1320
agtttcacaa tctcccaaag agtttcacta gtttgggacc aagtgctcaa ggacaagatt 1380
ctgtgggaac atttaactgt aacacacttc ttagcacaac tctgagctat gtaattttgg 1440
gcagtgccat gaaccctaaa agcctcgaat tatcattgta aaactaagat aaaactttgc 1500
aagataatca tgaatggcta agttaaaaga cacataaaag taattagcag agtgtttggc 1560
ctcgttttta tatgcagtca atggcagttc ttttagtatc aataaccttt atggcttaca 1620
gccatcctcc aaaaattatg acgagcagaa atctcctatg gatgttaacg tgcccctcag 1680
ttaggcaaag attggtccat actgaatgta gacttggtcc ttcaaatgga attatgaaaa 1740
caaaacacca aaaaaaaaaa aacccaaaaa aaaacaaaaa accccaaatt tctaaagacc 1800
taatgtcttt agaccatgtg gcagcaaaat gcaactccag cctcttgtct atcaaatccc 1860
aaggtctgga acggctcatt ttaaaaggca aattgattga attcagaacc actcaaggca 1920
ttcgtgaggc atgtctttag gtatgtgtct atgacagcat tctctggaaa ggattggctt 1980
agacccaccc tgaaaatgag tagctgcgac atcccctggg ctggatccag aactaattaa 2040
ggagaatacg gatatagaca caccttccct ccataaagaa cctgagacac aagcaaaact 2100
aatccctttc tcctttaagt tgctgcttgt caaagacttg gtcacagtaa ggagaaaaga 2160
ctatttcatt ttgcatatcc tatctgtggc ttgctgtaaa attaatgaag ttaactaagt 2220
agtgctgttc cagcctctgt tggaggcacg tgtatattat aggatatgac ctacataaat 2280
ctacctcttt ttttcctatt gttaggatcc caacagaaga ccaaagaatt ctgccatgtc 2340
tactgcatga gactccgttc tggcctcacc ataagaaagg agactagtta ttttaggaaa 2400
gaacccacga aaagatattc actaaaatcg ggtaagtaca tttctggaaa gactgatggg 2460
catctatttg cttttacttt ccatacacac acacacaaca cacacacaca cacacacaca 2520
cacacacaca cacacacacg cacacacaca cacaattgtt tttcttacct aaattctcct 2580
tgaggaaaag aatacagatg ataatgtgtt ggccatttta gaaagggttt ttctatttta 2640
gaatttctaa ataaatattc aaaaagtcta ttctagaatc cactttagaa atggatacac 2700
tggtgagtaa aaacagaaga cacaagatta tgtgtaaata tgtaatcatg tggtgtgata 2760

-continued

```
ttttgtaata tagaggaaac aaactaaatg gttcatagtg gctgctttgg aaggcagtaa   2820
ctgtggtgag tggctttctg tttatttgtt tgtttgtttc ttcctttggt gtgctctact   2880
ggagtgcaaa tggtcttcac tttacgtcat tattaaggag gaattgatcc cattagacca   2940
ttgggtggcc acagccctag gatcacttac caccgtcgcc atattggcca tcaaaaaaga   3000
tagcatattg gcacaatgaa gattgctgac tcagcccaag ccccactact gtcttgcagg   3060
taccaagcat gaagagaact tctctgccta tccacgggat tctaggaaga gatccttgct   3120
tggcagtatc caagcatttg ctgcgtctgt tgacacattg agcatccaag gtatgactgg   3180
tcatagggga tgtgtggggt gaggtgggag atagcacatg gggccttggc aagggctatt   3240
gcatagagca aactcaggag tatgtcttca tatgtattag aaacgtttgt ttcctgcttg   3300
ggtaccagtt cagtggttat ccaaattggg tgtggtggag ctgtgcctat ttaatctatg   3360
gttagcattc cacttgtatt ttgaaatact tgctataggt tgggagcatg tcttcatcag   3420
tcctgataaa tgtaatatcc ttggagagag gaaaaaaaca aagcaccagt ccccacattt   3480
caaaatgttc accatgaaag aaaataaagg aactatcttt taaaataaca tgatgtggct   3540
tgaagagtag tttaaagttt ttgaccattt ttgctgcgtt ctaagtaaaa tggtaattat   3600
caagaagtga agagaaccca gggcgtgtag ttcagtggta gaacatttgc ctcatgtgcc   3660
aggctctgca tgtagtctct atcaatgtgg gaaaaattca aagtgagggt tgggcataat   3720
ggcatataat ctccatccca gaatggggga ggcaggtgaa ttccttgggt tcaggtctgc   3780
ctggtctaca cagtgagtcc cagaacagtt agagttatat agtgagaaac tgtctcaaag   3840
acaaacaaaa ggccaaatta aataattaac aaattagcag ccccatcact aaggaatcgt   3900
gattaagaat cacatattgc cattctaata tatattattt ttatatgtga tcttatataa   3960
aacaacttag aatgtattta tgtatagtgt gtatatatat tatatatata tatatataat   4020
atatacttag tatatgttta atataaatac attaacctcc tggtcaatat tcagtttctc   4080
acaaactgga tttaaattac tttagatgtt tagatgttta gatgtttaga tgtttagatg   4140
ttcacatgca aattcttttct attttgtaca gtaaatttga atgtaggacc ctcagatggg   4200
tccaagtctg cttcagttta cccatatatg cttttaaaat gttatcaagt gctctgtatg   4260
tgtttcgatt gtccgggcaa aagcagaact agtttacatc tgcatccccc tagaccagtg   4320
actcaatctt cctaaatgct gtaacccttt aacatagttc tgcacgctgt ggtgacccca   4380
accataacct tactcttgtt gctacatcat aactgcaact ttgctactgt tatgaatcct   4440
aatgcaaata tctggtctgt aagatatctg atatgcaatc cctgtaaagg gatcatttaa   4500
cccacaaaag gtctggacca ccaggttgag aaacactgcc ctagagtgtt ggaaatctct   4560
aagtgatcat gctttataaa ggggaataca ttcacctatg tcttccaaaa catgaccatt   4620
ctttgcagct gtcccctaga ctgtgggaag gtaagaaaag gagctaccct cctcgtcctc   4680
accccaactg tgcaggaagg taacaccttt aatcccaccc tggtatcagc tatggtactt   4740
agcttttgcc tatgttacaa tgacaaagta gagctcacac taaagaccaa aactcttcag   4800
aggaagtaat tcatataaat aaccaagaga acggttcata gaatcctttg tgtttttttat   4860
tcttaatgac aggaacttca cttttaacac agtctcctgc ctccctgagt acatacaatg   4920
accaatctgt tagttttgtt ttggagaatg gatgttatgt gatcaatgtt gacgactctg   4980
gaaaagacca agagcaaggt agagtatctc ctcacgtcta tacttagtaa tgactggcaa   5040
ggtttaaaaa aaaaaaatct accaagttat caacagtgga ttaactgagc tattcaacag   5100
```

-continued

```
cagcaagttt caccatcttt ggtaatttta gtccttccta tgtcaagaag gtctcagtgt   5160
agtcacattc ttcagggaat aaatcagaca ttgagaaata cctattgaga aatacagaaa   5220
gagggactac atgtatctac aaatgctgaa taataagatc ttgttcacct tttcagtgtc   5280
cccaaagcat agtcttttgt gaaagattat ccctttgtca taaacaatac cacctgcata   5340
ttggggaatc catcagagca gaatatattt taagatcttt ctaagaatca ctaaagttcc   5400
gctttttgg tatatgacaa aaggagaggg agtttgtgtt ccccgcccag cccagcccca   5460
ggacgggatg gaaccgaaac cttttgatac gttcctctgt cacccagtga cacccaatgt   5520
tgtctttcag accaggtgct actacgctac tatgagtctc cctgtcctgc aagtcaatca   5580
ggtaatgtag aggcaggggg agggggtggt gtttgcattc tcatccagaa caaagctgaa   5640
tctgaagtag cccgtggtta tcatgaggtt cagaaggtta tcttcaaccc cacactcatt   5700
gtaaaacctt acctcatcta cttctgaatt agtaggagaa aagcctagct gcacttataa   5760
tagtacagcc ataatagtac agcccatctc agccaagact caaaagattc tgctcaaagg   5820
ttgcccagaa gcagttcctt ctacatcatc agtccatcca tgcataatgg ctcaccacta   5880
tggccagtca gcaagagaca ggaaggcagg tgaatacata tgtcttccgc ttcagggcac   5940
aattgtgtac cacgtgtctg cttatcttca gttggtcaga acttagtctg agagcaacag   6000
gaggagaaaa gttctattat ctgttatcta ttagaggaca gctctcagca gcttcccatg   6060
aacagaggga agcaggtgac caaagcagta tccattggca tcagttgaat tacaaaagat   6120
cagaacaaca acagaaagta aaaactaaaa cctctcctca gaaagattta gaaagactct   6180
tgggctggcc ttggtggtgc acatctttaa tcccagcact caggaggcca aggcaagcag   6240
atctctgagt tcaaagccag cctgacctac agagtgagtt tcaggacaga tagggccaca   6300
caaagaaacc ctatcttggg ggaaggaaga aataaaagga aggaaggaag ggagggaagg   6360
gaagggaagg gaagggaagg gaagggaagg gaagggaagg gaagggaagg aagaagggag   6420
ggagggagga agggaaggag gaaagaagga agagagggag gaaagaagga aggaaggaag   6480
gaaggaagga aggaaggaag gaaggaagga aggaaggaag gactacctgg tatttgggtg   6540
caaatacttt taaatggatt agtgagctat tttcatttgc aactgaaatt ctttgagtta   6600
agttaagatg agttacaaga cttagaattt ttgatttgta atttctttgt cttactttta   6660
attgataggt aaaattgtat taatcatgaa ccacagatga tttttgcttt ggagcaagcg   6720
atattttttt taaaaagatt ttatttctat ttaatgggta tgaatgtttt gcttgcatgc   6780
atgtaagcgc ttgagatgct tatagttgtg tagaaagcta gaagacagca ctggatgtcc   6840
tgtaacttat gggctctggg aactgaatgc aggtcctctt gcaagggcat caagtgctca   6900
tgacgaagga agtatctctc tagtcccata gcaggagttt tttttttttt taaagattta   6960
tttattgatt atatgtaagt acactgtagc tgtcttcaga cactccagaa gagggcatca   7020
gatttcatta gggatggttg tgagccacca tgtggttgct gggatttgaa ctctggacct   7080
tcagaagagc aatcgggtgc tcttacccac tgagccatct caccagccca tagcaggagt   7140
tttgaggtat ctattgtctc tgtctaatag agagatcaaa tgaggccaag tggcagctgt   7200
atcacctcac cttataattt tcattttaag gcgacggtgt ggatgggaag aagctgatgg   7260
tgaacatgag tcccatcaaa gacacagaca tctggctgca tgccaacgac aaggactact   7320
ccgtggaggt aacagaaata tgaccctatg acggccacac ttggttctac ctgttaacgt   7380
aaaatagatg ttagatgtta gggcaatttt gaaggcagaa gtacacactg ttgaaaataa   7440
actacagtca gtcacttcta atgacttgct tgggagtagg gaagggagag aagtgtggtc   7500
```

```
ttgttgctac aagtctggtc tccagcaaca acacagaatc actggagaac ttgtcagaaa   7560

gcaggatttc cggctccccc cacatccgaa tcagatctaa agtctccagg acaggaactt   7620

catcccttca ccacagtttg agaggcactt ctgcacagag tgagtcacag cctttccatt   7680

tggctatgtt cttccagaat tgttttagga ttatttattt tatgcatatg aatgtactgt   7740

cactgtgttc ggtcacacca gaagagggca tcagatccca ttacagatgg ttgtgagcca   7800

ccatgtggtt gctgggaatt gagctgagga cctctggaag agcagttggt gctcttaacc   7860

gctgagccat ctctccagcc ctggagatat atagtttctg actccaagtc tgtcaagggg   7920

aaggcagcaa atgtgtccat acatcagcag tttggggcag cattacattc tacatctggt   7980

ccgttcttgc tcagcaaaca gcaggtgtac atcagccagg acgaaaaaaa aaattctgat   8040

catgtaaaga acaaacaggc cagagtgaga aggaaggaag gaagggagga aggacatggg   8100

agaacataat aacgaagatg atttctataa atatatacca tttcaaagca atccagccac   8160

ataagacatc aacacaaaca gtccacaaag accagcactc ttctcaggag aatactctca   8220

ggtgtacatg atgcaaaatc tagcagaaag aaagcctcaa aagtaacagt gggctgccat   8280

ggcacatcaa gttcttgctt accatttcct aagccctgtc tctttaatcc tcacagcaaa   8340

tttatatgga aaaattgcct tggtcagcta ttgtgcaaca aactatcaca aaactcattg   8400

gattaaaata ataatcacat ataggtcctc agcaactgag agctcattcc gacgacctga   8460

gttggctccc cagtattcat tggcaggcga ctcacaacac ctgtagctct cgctccaaga   8520

cagtcaggtg cctctggcct ccatagacat ctacacttat gtgcacacac tcagacatag   8580

ccacatacac ataatttaaa ataaattctt aaaaataaca caaattaaaa acaataatct   8640

gtatttaaat gagcttaatt taattgaaca acttagttta acaatcaact taattaaaat   8700

atgtctgtat ttaaactgac aatgaacgaa cctagagggc gtgtccacag agagttctgg   8760

ctaaactgaa aagtccaggt ttactagata catactagac agacatgttc tcatggcaaa   8820

aacagagggg aacaaatctg gatgttttgc ggtagtttgt tgcacagaag ctgaccaagg   8880

taattattcc atataaactt gctgtgtgaa ttaaagagat ggggtttgtg acgtatgaag   8940

gaaattgacc tggtcagtct ctgccaagct gcttatccac tctccacaaa tcgctttcac   9000

ctcttccatg cagcctctct attccctcca ctgctcattt ctccctcctc gactcagtac   9060

aaacttccta gaaagttcaa gctataagtg atcagtcccc ccatggatgc tgacccagga   9120

aggcaatggt agctctggac tccccattca caccttggtt tcttctcttc ttccctcagc   9180

ttcaaagggg tgacgtctcg cctccggaac aggccttctt cgtccttcac aaaaagtcct   9240

cggactttgt ttcatttgaa tgcaagaatc ttcctggcac ttacatagga gtaaaagata   9300

accagctggc tctagtggag gagaaagatg agagctgcaa caatattatg tttaagctct   9360

cgaaaatcta a                                                        9371
```

<210> SEQ ID NO 2
<211> LENGTH: 10697
<212> TYPE: DNA
<213> ORGANISM: Artificial Sequence
<220> FEATURE:
<223> OTHER INFORMATION: Targeting vector for mouse IL-33

<400> SEQUENCE: 2

```
tagctctcca ccggggctca ctgcaggaaa gtacagcatt caagaccagc tatttcctgt     60

ctgtattgag gtgagtgcca ggtcaatctc tctgtttctg aggggaacca atagtagcat    120
```

-continued

```
ctatcagctc tcaaatgatt ctgatataaa gagagaaaag acttgttact ggagaaagtg    180

gcttgtttat cagaatggga tttgaaacca gttctgggtt atacttttag ttctgcaatt    240

gtgataaaga tgctgacagt cttggtcgat gtatctgtcc ttaatgctca ctccttagtt    300

tcttatctgt tcaaccacgc aggctagtag tcctttagag caaagttctt ctacatgagt    360

ttgctcaagc tcgtccaagg gaggacgaaa gggaagggaa ggttaggaga tcaaataatt    420

aactgaagat agagaaaggc aaaggcaggc agggcgtctc agtgaggggc tgctggtatt    480

gttattatgt taacatgcat gaactctaag tctccaagaa gagaggctat cgactgcaac    540

acacaggttt atttaaaaga caattttaat gactagaaaa acattgtttc taggacacat    600

gcaccctctg gtgaaagaga aaacagaaat cagcactgtt tcaggaagca gctcagaagc    660

tcagcactag cagtgagcaa gggacctcaa ttcctcctgg tacaggcagg ctattattta    720

aactgtttcc tgcccaactg aaaatctgac ctttatgtgg ttagctaatc ctattacccc    780

acacagaagg cttaaaaatt aactattctg taaaagctat aactctgctt taaaggaaat    840

tatgtattct gagccagaaa ggatgactga ccattgtggc ttagtagtat ggattcaagt    900

taccctaaat gatacattcc taagtgaaag ccattacatt aagggtttca ggcaaagaat    960

aaaggccacc atacaccaat gtattcaata actgcattag tcataacacg ttcgacacac   1020

agaagacaca agaaggagga ggtctctctt gtaggttttg aatgcttgca gcttcttagc   1080

tttgtgctat gcataaacag cccattctga gagtatcaaa tcagatgcca ttattaaaag   1140

aaatggctgt ttacacaaaa agcctaagac agccagagat aaagtttggc tcttgatcat   1200

tgaccaatga tcaagacaat gacaatattt tactcagtga acgagaagag tacgtgggat   1260

tatttaaccc agccgcagct tcttcaggga actctgcctt atgttagtta acatcttccg   1320

aaatttatta ttactatttc aagaatatta atatttcaag aagctggcca tttgctttga   1380

gtataagaag ggctgagtgt ttgaaataaa ataccaagtt ctaatccacc cgactcccac   1440

cccccaagcc gcaccccgca cctcctcgaa gttgtcaact gatgcagttg ttggatgtat   1500

tggctggcat atggttgcct ttgttctttg cctgaaagcc ttcatgcgac tgctttccgc   1560

ttaggagtgc attgtttagg gaaacttgaa tcaatgctac taagccatga tcagctatca   1620

tcgctggctc agaataaatg gttcccttca aagcagagtt gtaactttta tagagtagtt   1680

aatttttaat ccttttgaac aaaagagaga gagagagagg atgataatgg agggagagag   1740

aagagataac agttttagtt tcattggggg ggtggtacag gataagagat aagttctact   1800

ttcattcttc tacacatgga tatccagctc tcccagttta aaaaaatttt taaggctata   1860

tttttctgat gtgtttttga tgccactagc aagaattaga cggttctatt ggcctgagta   1920

tgacataatt atattttgat ttttaaaaaa tttaagaaaa aatagacaat gtgttaaggt   1980

tgaaacagtg tggggaagat aacaagattt aaaactcaaa tgtaaaagaa gtagataaaa   2040

ttagacagaa gagggataaa aatgttttta aaaatcaaaa taataagtaa tagttttaaa   2100

tgagaggaaa ataaaaagag agacggaagc acctttccgg gtctgtgagc agagggcaga   2160

gggctagagc ttgctcccac taagctggct agaatagcga ggccagttga gagcacccat   2220

cctcagcctc agggctgtgt ttactctaga ctgtaaaagc gtagatgctt tcttcctttg   2280

cacttatggg gccatggcat cccccgacga tgtctacatt ccttaggctt gggcaggtta   2340

tcattcactg aggctctctg gagtccgcga ctgtggcaaa gtccacctag ttcacctcag   2400

aatgaaggga gcaaacggct ctcctagtta tgtccagatg gaagagcaat cagcctgtcc   2460

tggtttataa gtaatcttca gctacctgct tggaggcctc agtcatcccc aatcccagga   2520
```

```
gctgagtagt cctcgccacc agagggcggg agcactgatc actgtgtctt ccttcctcaa   2580
ctgagcaggc tccccgtaat tgaaacttct cattggttcg ttcatccgaa ccaatcccctt   2640
ccaggattgc ctcatagccg gtcactatgg cagcgttccc aggcatcctg atttggcacc   2700
tgtctgtatt ttctgatctt cagagttgct gctggtcaca acacttttaa actaccggag   2760
agtgacggtg tggcgtcttt actctaggca gcagtggaca ggaactcgcc cttagaccta   2820
atttctgccc tggcttgtga gaactgtact gttaaccatg ggtttctccc gctgcgctgc   2880
gagcagcgca attctattct tctggtagcc taaacccaga tgaacttgtg attgttgctc   2940
cctccctcct aatccttccc agtccctctc cccatccccc accaatgcct ggaaccggga   3000
ctggagctct ggactgcttc ctacttcgtg ttatcttttt gtttctccat gagttttaat   3060
tgccctgttg tttttgttgt tgttttggtt ttccccccttt atgcccagtg atttctccac   3120
tagatctcct tgggctttgg tttgtccttt gttaccctgg tctttgaact tgtgagaaaa   3180
tcggcaacct tactccattt attcttgagg aaccatgctt aatcttgatc actgcctgcc   3240
attactcttt ttaaacattc agctggtgcc aaatctgacc cgaggaaacc ctccacggtg   3300
gctcccacat gcttttgaca caaactcatt tagtttttta atagctggac gttttctggc   3360
ataacgtgtt ttatggtcat tattactttc ctgaccacga atctggagtc aaagttcctt   3420
ccagtggaga aaatatttag aaaataaaat gtgtacacac actgcttgtt taatactgac   3480
tcaaatctaa catcgcaggg catttgcctt ggcttctgag ttacgtattt atatttctta   3540
ccccccctaca gtgagaaatc atacaagatc agtatcgcta tttttttttt ttttttgcta   3600
tatactacaa caaaacagta ctgagatttc aacacaaaca tggcattaac actaagacta   3660
ctcagcctca gatttctctg tgctttcatt actttattct ttgattctat ggctagattc   3720
tagcctaaat gtagagtcag aatactatgc tgaattttat tctccccccct cccccctgta   3780
tggctatcag tttcatggtg agatagccaa ggttgcttct gatgacttca ggtccatata   3840
gttggattaa tgttatattt caatcccaca gaaacctgaa aatggacaa caccgaggac   3900
gtcatcaagg agttcatgca gttcaaggtg cgcatggagg gctccgtgaa cggccactac   3960
ttcgagatcg agggcgaggg cgagggcaag ccctacgagg gcacccagac cgccaagctg   4020
caggtgacca agggcggccc cctgcccttc gcctgggaca tcctgtcccc ccagttccag   4080
tacggctcca aggcctacgt gaagcacccc gccgacatcc ccgactacat gaagctgtcc   4140
ttccccgagg gcttcacctg ggagcgctcc atgaacttcg aggacggcgg cgtggtggag   4200
gtgcagcagg actcctccct gcaggacggc accttcatct acaaggtgaa gttcaagggc   4260
gtgaacttcc ccgccgacgg ccccgtaatg cagaagaaga ctgccggctg ggagccctcc   4320
accgagaagc tgtaccccca ggacggcgtg ctgaagggcg agatctccca cgccctgaag   4380
ctgaaggacg gcggccacta cacctgcgac ttcaagaccg tgtacaaggc caagaagccc   4440
gtgcagctgc ccggcaacca ctacgtggac tccaagctgg acatcaccaa ccacaacgag   4500
gactacaccg tggtggagca gtacgagcac gccgaggccc gccactccgg ctcccagaaa   4560
agatattcac taaaatcggg taagtacatt ataacttcgt atagcataca ttatacgaag   4620
ttatcgcaca cattccacat ccaccggtag gcgccaaccg gctccgttct ttggtggccc   4680
cgtcgcgcca ccttctactc ctcccctagt caggaagttc ccccccgccc cgcagctcgc   4740
gtcgtgcagg acgtgacaaa tggaagtagc acgtctcact agtctcgtgc agatggacag   4800
caccgctgag caatggaagc gggtaggcct ttggggcagc ggccaatagc agctttgctc   4860
```

```
cttcgctttc tgggctcaga ggctgggaag ggtgggtcc gggggcgggc tcaggggcgg   4920
gctcaggggc ggggcgggcg cccgaaggtc ctccggaggc ccggcattct gcacgcttca   4980
aaagcgcacg tctgccgcgc tgttctcctc ttcctcatct ccgggccttt cgacctgcag   5040
cagcacgtgt tgacaattaa tcatcggcat agtatatcgg catagtataa tacgacaagg   5100
tgaggaacta aaccatggga tcggccattg aacaagatgg attgcacgca ggttctccgg   5160
ccgcttgggt ggagaggcta ttcggctatg actgggcaca acagacgatc ggctgctctg   5220
atgccgccgt gttccggctg tcagcgcagg ggcgcccggt tctttttgtc aagaccgacc   5280
tgtccggtgc cctgaatgaa ctgcaggacg aggcagcgcg gctatcgtgg ctggccacga   5340
cgggcgttcc ttgcgcagct gtgctcgacg ttgtcactga agcgggaagg gactggctgc   5400
tattgggcga agtgccgggg caggatctcc tgtcatctca ccttgctcct gccgagaaag   5460
tatccatcat ggctgatgca atgcggcggc tgcatacgct tgatccggct acctgcccat   5520
tcgaccacca agcgaaacat cgcatcgagc gagcacgtac tcggatggaa gccggtcttg   5580
tcgatcagga tgatctggac gaagagcatc aggggctcgc gccagccgaa ctgttcgcca   5640
ggctcaaggc gcgcatgccc gacggcgagg atctcgtcgt gacccatggc gatgcctgct   5700
tgccgaatat catggtggaa aatggccgct tttctggatt catcgactgt ggccggctgg   5760
gtgtggcgga ccgctatcag gacatagcgt tggctacccg tgatattgct gaagagcttg   5820
gcggcgaatg ggctgaccgc ttcctcgtgc tttacggtat cgccgccccc gattcgcagc   5880
gcatcgcctt ctatcgcctt cttgacgagt tcttctgagc gggactctgg ggttcgaata   5940
aagaccgacc aagcgacgtc tgagagctcc ctggcgaatt cggtaccaat aaaagagctt   6000
tattttcatg atctgtgtgt tggtttttgt gtgcggcgcg ataacttcgt atagcataca   6060
ttatacgaag ttattcttac ctaaattctc cttgaggaaa agaatacaga tgataatgtg   6120
ttggccattt tagaaagggt ttttctattt tagaatttct aaataaatat tcaaaaagtc   6180
tattctagaa tccactttag aaatggatac actggtgagt aaaaacagaa gacacaagat   6240
tatgtgtaaa tatgtaatca tgtggtgtga tattttgtaa tatagaggaa acaaactaaa   6300
tggttcatag tggctgcttt ggaaggcagt aactgtggtg agtggctttc tgtttatttg   6360
tttgtttgtt tcttcctttg gtgtgctcta ctggagtgca aatggtcttc actttacgtc   6420
attattaagg aggaattgat cccattagac cattgggtgg ccacagccct aggatcactt   6480
accaccgtcg ccatattggc catcaaaaaa gatagcatat tggcacaatg aagattgctg   6540
actcagccca agccccacta ctgtcttgca ggtaccaagc atgaagagaa cttctctgcc   6600
tatccacggg attctaggaa gagatccttg cttggcagta tccaagcatt tgctgcgtct   6660
gttgacacat tgagcatcca aggtatgact ggtcataggg gatgtgtggg gtgaggtggg   6720
agatagcaca tggggccttg gcaagggcta ttgcatagag caaactcagg agtatgtctt   6780
catatgtatt agaaacgttt gtttcctgct tgggtaccag ttcagtggtt atccaaattg   6840
ggtgtggtgg agctgtgcct atttaatcta tggttagcat tccacttgta ttttgaaata   6900
cttgctatag gttgggagca tgtcttcatc agtcctgata aatgtaatat ccttggagag   6960
aggaaaaaaa caaagcacca gtccccacat ttcaaaatgt tcaccatgaa agaaaataaa   7020
ggaactatct tttaaaataa catgatgtgg cttgaagagt agtttaaagt ttttgaccat   7080
ttttgctgcg ttctaagtaa aatggtaatt atcaagaagt gaagagaacc cagggcgtgt   7140
agttcagtgg tagaacattt gcctcatgtg ccaggctctg catgtagtct ctatcaatgt   7200
gggaaaaatt caaagtgagg gttgggcata atggcatata atctccatcc cagaatgggg   7260
```

```
gaggcaggtg aattctaacc tcgacccgct ctagaactac gatccagaca tgataagata   7320
cattgatgag tttggacaaa ccacaactag aatgcagtga aaaaaatgct ttatttgtga   7380
aatttgtgat gctattgctt tatttgtaac cattataagc tgcaataaac aagttagatc   7440
ctagtggatc tgcattccac cactgctccc attcatcagt tccataggtt ggaatctaaa   7500
atacacaaac aattaggaat cagtagttta acacattata cacttaaaaa ttttatattt   7560
accttagagc tttaaatctc tgtaggtagt ttgtccaatt atgtcacacc acagaagtaa   7620
ggtttccttc acaaagagat cgcctgacac gatttcctgc acaggcttga gccatatact   7680
catacatcgc atcttggcca cgttttccac gggtttcaaa attaatctca agttctacgc   7740
ttaacgcttt cgcctgttcc cagttattaa tatattcaac gctagaactc ccctcagcga   7800
agggaaggct gagcactaca cgcgaagcac catcaccgaa ccttttgata aactcttccg   7860
ttccgacttg ctccatcaac ggttcagtga gacttaaacc taactctttc ttaatagttt   7920
cggcattatc cacttttagt gcgagaacct tcgtcagtcc tggatacgtc actttgacca   7980
cgcctccagc ttttccagag agcgggtttt cattatctac agagtatccc gcagcgtcgt   8040
atttattgtc ggtactataa aaccctttcc aatcatcgtc ataatttcct tgtgtaccag   8100
attttggctt ttgtatacct ttttgaatgg aatctacata accaggttta gtcccgtggt   8160
acgaagaaaa gttttccatc acaaaagatt tagaagaatc aacaacatca tcagggtcca   8220
tggcgaggac ctgcaggtcg cagatcctga acggcagagg ttacggcagt ttgtctctcc   8280
cccttccggg agccaccttc ttctccaacc gtcccggtcg cgctctcggc gcttctgagg   8340
agagaactgg ctgagtgacg ccctttatag attcgccctt gtgtcccgcc cttcctttcc   8400
cgccctccct tgcgctacgg ggccgcccgc accggcctac acggagcgcg cgcggcggag   8460
ttgttcggtc cggccgccac cgcggtggag ctccagcttt tgttcccttt agtgagggtt   8520
aatttcgagc ttggcgtaat catggtcata gctgtttcct gtgtgaaatt gttatccgct   8580
cacaattcca cacaacatac gagccggaag cataaagtgt aaagcctggg gtgcctaatg   8640
agtgagctaa ctcacattaa ttgcgttgcg ctcactgccc gctttccagt cgggaaacct   8700
gtcgtgccag ctgcattaat gaatcggcca acgcgcgggg agaggcggtt tgcgtattgg   8760
gcgctcttcc gcttcctcgc tcactgactc gctgcgctcg gtcgttcggc tgcggcgagc   8820
ggtatcagct cactcaaagg cggtaatacg gttatccaca gaatcagggg ataacgcagg   8880
aaagaacatg tgagcaaaag gccagcaaaa ggccaggaac cgtaaaaagg ccgcgttgct   8940
ggcgtttttc cataggctcc gcccccctga cgagcatcac aaaaatcgac gctcaagtca   9000
gaggtggcga aacccgacag gactataaag ataccaggcg tttccccctg gaagctccct   9060
cgtgcgctct cctgttccga ccctgccgct taccggatac ctgtccgcct ttctcccttc   9120
gggaagcgtg gcgctttctc atagctcacg ctgtaggtat ctcagttcgg tgtaggtcgt   9180
tcgctccaag ctgggctgtg tgcacgaacc ccccgttcag cccgaccgct gcgccttatc   9240
cggtaactat cgtcttgagt ccaacccggt aagacacgac ttatcgccac tggcagcagc   9300
cactggtaac aggattagca gagcgaggta tgtaggcggt gctacagagt tcttgaagtg   9360
gtggcctaac tacggctaca ctagaaggac agtatttggt atctgcgctc tgctgaagcc   9420
agttaccttc ggaaaaagag ttggtagctc ttgatccggc aaacaaacca ccgctggtag   9480
cggtggtttt tttgtttgca agcagcagat tacgcgcaga aaaaaaggat ctcaagaaga   9540
tcctttgatc ttttctacgg ggtctgacgc tcagtggaac gaaaactcac gttaagggat   9600
```

-continued

```
tttggtcatg agattatcaa aaaggatctt cacctagatc cttttaaatt aaaaatgaag   9660

ttttaaatca atctaaagta tatatgagta aacttggtct gacagttacc aatgcttaat   9720

cagtgaggca cctatctcag cgatctgtct atttcgttca tccatagttg cctgactccc   9780

cgtcgtgtag ataactacga tacgggaggg cttaccatct ggccccagtg ctgcaatgat   9840

accgcgagac ccacgctcac cggctccaga tttatcagca ataaaccagc cagccggaag   9900

ggccgagcgc agaagtggtc ctgcaacttt atccgcctcc atccagtcta ttaattgttg   9960

ccgggaagct agagtaagta gttcgccagt taatagtttg cgcaacgttg ttgccattgc  10020

tacaggcatc gtggtgtcac gctcgtcgtt tggtatggct tcattcagct ccggttccca  10080

acgatcaagg cgagttacat gatcccccat gttgtgcaaa aaagcggtta gctccttcgg  10140

tcctccgatc gttgtcagaa gtaagttggc cgcagtgtta tcactcatgg ttatggcagc  10200

actgcataat tctcttactg tcatgccatc cgtaagatgc ttttctgtga ctggtgagta  10260

ctcaaccaag tcattctgag aatagtgtat gcggcgaccg agttgctctt gcccggcgtc  10320

aatacgggat aataccgcgc cacatagcag aactttaaaa gtgctcatca ttggaaaacg  10380

ttcttcgggg cgaaaactct caaggatctt accgctgttg agatccagtt cgatgtaacc  10440

cactcgtgca cccaactgat cttcagcatc ttttactttc accagcgttt ctgggtgagc  10500

aaaaacagga aggcaaaatg ccgcaaaaaa gggaataagg gcgacacgga aatgttgaat  10560

actcatactc ttcctttttc aatattattg aagcatttat cagggttatt gtctcatgag  10620

cggatacata tttgaatgta tttagaaaaa taaacaaata ggggttccgc gcacatttcc  10680

ccgaaaagtg cctcgag                                                 10697


<210> SEQ ID NO 3
<211> LENGTH: 22
<212> TYPE: DNA
<213> ORGANISM: Artificial Sequence
<220> FEATURE:
<223> OTHER INFORMATION: PCR Primer (Oligonucleotide A)

<400> SEQUENCE: 3

tagaaagagc ccagtgttaa gc                                              22


<210> SEQ ID NO 4
<211> LENGTH: 18
<212> TYPE: DNA
<213> ORGANISM: Artificial Sequence
<220> FEATURE:
<223> OTHER INFORMATION: PCR Primer (Oligonucleotide B)

<400> SEQUENCE: 4

ggcttgccct cgccctcg                                                   18


<210> SEQ ID NO 5
<211> LENGTH: 19
<212> TYPE: DNA
<213> ORGANISM: Artificial Sequence
<220> FEATURE:
<223> OTHER INFORMATION: PCR Primer (Oligonucleotide C)

<400> SEQUENCE: 5

cacctgcgac ttcaagacc                                                  19


<210> SEQ ID NO 6
<211> LENGTH: 21
<212> TYPE: DNA
<213> ORGANISM: Artificial Sequence
```

-continued

```
<220> FEATURE:
<223> OTHER INFORMATION: PCR Primer (Oligonucleotide D)

<400> SEQUENCE: 6

acgattcctt agtgatgggg c                                              21


<210> SEQ ID NO 7
<211> LENGTH: 21
<212> TYPE: DNA
<213> ORGANISM: Artificial Sequence
<220> FEATURE:
<223> OTHER INFORMATION: PCR Primer (Oligonucleotide E)

<400> SEQUENCE: 7

gttgcttctg atgacttcag g                                              21


<210> SEQ ID NO 8
<211> LENGTH: 20
<212> TYPE: DNA
<213> ORGANISM: Artificial Sequence
<220> FEATURE:
<223> OTHER INFORMATION: PCR Primer (Oligonucleotide F)

<400> SEQUENCE: 8

gcaatagccc ttgccaaggc                                                20


<210> SEQ ID NO 9
<211> LENGTH: 21
<212> TYPE: DNA
<213> ORGANISM: Artificial Sequence
<220> FEATURE:
<223> OTHER INFORMATION: PCR Primer (Oligonucleotide G)

<400> SEQUENCE: 9

tgctgttcca gcctctgttg g                                              21
```